(12) United States Patent
Ma et al.

(10) Patent No.: US 8,591,962 B2
(45) Date of Patent: Nov. 26, 2013

(54) COMPOSITION FOR PREVENTING AND TREATING INFLUENZA-VIRUS-INDUCED DISEASES

(75) Inventors: Jin Yeul Ma, Daejeon (KR); Young Ran Um, Gyeongsangbuk-do (KR); Ji Hye Lee, Gyeongsangbuk-do (KR)

(73) Assignee: Korea Institute of Oriental Medicine (KR)

( * ) Notice: Subject to any disclaimer, the term of this patent is extended or adjusted under 35 U.S.C. 154(b) by 0 days.

(21) Appl. No.: 13/508,296

(22) PCT Filed: Jan. 7, 2010

(86) PCT No.: PCT/KR2010/000107
§ 371 (c)(1),
(2), (4) Date: Jul. 17, 2012

(87) PCT Pub. No.: WO2011/055881
PCT Pub. Date: May 12, 2011

(65) Prior Publication Data
US 2012/0276223 A1    Nov. 1, 2012

(30) Foreign Application Priority Data
Nov. 5, 2009  (KR) ........................ 10-2009-0106407

(51) Int. Cl.
*A01N 65/00*    (2009.01)
(52) U.S. Cl.
USPC ........................................................ 424/725
(58) Field of Classification Search
None
See application file for complete search history.

(56) References Cited

U.S. PATENT DOCUMENTS

| | | | |
|---|---|---|---|
| 2002/0168426 A1 | 11/2002 | Shen et al. | |
| 2010/0255127 A1 | 10/2010 | Norimoto et al. | |
| 2012/0040026 A1 | 2/2012 | Norimoto et al. | |
| 2012/0070514 A1 | 3/2012 | Norimoto et al. | |

FOREIGN PATENT DOCUMENTS

| | | |
|---|---|---|
| CN | 1 179 965 A | 4/1998 |
| CN | 1 513 524 A | 7/2004 |
| CN | 1 799 593 A | 7/2006 |
| CN | 1 840 163 A | 10/2006 |
| CN | 101 088 533 A | 12/2007 |
| CN | 101181553 A | 5/2008 |
| CN | 101 279 028 A | 10/2008 |
| CN | 101 301 464 A | 11/2008 |
| CN | 101 390 995 A | 3/2009 |
| CN | 101 485 842 A | 7/2009 |
| CN | 101460484 A | 7/2009 |
| CN | 101 658 562 A | 3/2010 |
| JP | 03-66623 A | 3/1991 |
| JP | 6-199680 A | 7/1994 |
| JP | 7-173069 A | 7/1995 |
| JP | 2003-026585 A | 1/2003 |
| JP | 2004-262929 A | 9/2004 |
| JP | 2005-320323 A | 11/2005 |
| JP | 2008-184449 A | 8/2008 |
| JP | 2009-046391 A | 3/2009 |
| JP | 2009-242354 A | 10/2009 |
| KR | 10-1999-0085819 A | 12/1999 |
| KR | 100 295 395 B1 | 4/2001 |
| KR | 10-2006-0040418 A | 5/2006 |
| RU | 2 190 393 C1 | 10/2002 |
| WO | WO 03/045408 A1 | 6/2003 |
| WO | WO 2009/066712 A1 | 5/2009 |

OTHER PUBLICATIONS

European Search Report for European Patent Application No. 10828416.3 (Apr. 4, 2013).
Ying et al., *Livestock and Poultry Industry*, No. 2, 2005, pp. 8-9.
Hioki et al., "Bofutsushosan use for obesity with IGT: search for scientific basis and development of effective therapy with Kampo medcine," *J Trad Med*, 24(4):115-127 (2007).
Kim et al., "The Effect of Bangpunglongsung-San on Model of Allergic Rhinitis," *The Journal of Korean Oriental Medical Opthamology & Otolaryngology & Dermatology* (2006) 19 (1):21-30.
Suhr et al., "Antiviral Effects of Fermented *Loniceraeflos* on A Type Influenza Virus," *Korean J. Orient. Int. Med.* (2009) 30 (3): 465-480.
Choi et al., "Aucklandiae Radix has inhibitory effects of pro-inflammatory mediator in LPS-induced RAW 264.7 cell," *The Journal of Jeahan Oriental Medical Academy* (2009) 7 (1): 1-12 Abstract only.
International Search Report for corresponding International Application No. PCT/KR2010/000107 (Form PCT/ISA/210) mailed Dec. 6, 2010.
D.J. Alexander, "A review of avian influenza in different bird species," *Veterinary Microbiology*, 74(1-2):3-13 (2000).
Park et al., "Literature Review on Children's Sinusitus," *J. Korean Oriental Pediatrics*, 3(1): 23-40 (1989).
H. Shin, "Coronavirus Replication Inhibition by Herbal Extracts," Dissertation Submitted to the Graduate School of Ajou Univ, 37 pp, (2007).
Slemons et al., "Type-A Influenza Viruses isolated from Wild Free-Flying Ducks in California," *Avian Disease*, 18(1): 119-124 (1973).
Song et al., "Control and Prevention Strategies of Avian Influenza," *Korean J. Poult. Sci.*, 31(2): 129-136 (2004).
Suarez et al., "Comparisons of Highly Virulent H5N1 Influenza a Viruses Isolated from Humans and Chickens from Hong Kong," *J. of Virology*, 72(8): 6676-6688 (1998).
Ward et al., "Oseltamivir (Tamiflu®) and its potential for use in the event of an influenza pandemic," *J. of Antimicrobial Chemotherapy*, 55(Suppl. S1): I5-I21 (2005).
Webster et al., "Evolution and Ecology of Influenza A Viruses." *Microbiological Reviews*, 56(1): 152-179 (1992).

*Primary Examiner* — Michael Meller
(74) *Attorney, Agent, or Firm* — Merchant & Gould P.C.

(57) ABSTRACT

The present invention relates to a medicinal extract useful for preventing and treating influenza-virus-induced diseases, and to a pharmaceutical composition and health food including same. Derived from natural ingredients, the medicinal extract of the present invention is safe for humans, and can be used to prevent, treat, and alleviate symptoms of diseases induced by various strains of influenza viruses.

1 Claim, 2 Drawing Sheets

COMPOSITION FOR PREVENTING AND TREATING INFLUENZA-VIRUS-INDUCED DISEASES

This application is a U.S. National Stage Application under 35 U.S.C. §371 of International Patent Application No. PCT/KR2010/000107, filed 7 Jan. 2010, which claims the benefit of priority to South Korean Patent Application No. 10-2009-0106407, filed 5 Nov. 2009, the disclosures of all of which are hereby incorporated by reference in their entireties. The International Application was published in Korean on 12 May 2011 as WO 2011/055881. To the extent appropriate, a claim of priority is made to each of the above disclosed applications.

TECHNICAL FIELD

The present invention relates to a herbal extract useful for the prevention and/or treatment of influenza virus-induced diseases, more precisely, to a herbal extract that is very effective in preventing and/or treating influenza virus-induced diseases, particularly those infecting human.

BACKGROUND

Influenza virus is a RNA virus belonging to Family Orthomyxoviridae which causes inflammation in respiratory system. This is a highly infectious virus that infects others via direct communication through air from cough or saliva of the infected ones or via indirect communication through anything that is touched by the infected ones. The incubation period of this virus is 24~30 hours and serotype of the virus is divided as type A, type B, and type C. Type B and type C are confirmed to infect only human, while type A can infect not only human but also various species of mammals including horse, pig, and others, and also various species of domestic poultry and wild birds (Selmons et al., Avian Dis., 18(1), p. 119-124, 1974; Webster R G et al., Microbiol Rev., 56(1), p. 152-179, 1992).

The classification of serotype of type A influenza virus depends on the two kinds of proteins observed on the surface of the virus, which are Hemagglutinin (HA) and Neuraminidase (NA). Type A virus can be divided into 144 different serotypes (16 kinds of HA and 9 kinds of NA). HA aids the virus to be attached on somatic cells, while NA helps the virus to invade into the cells (Alexander D J, Vet. Microbiol., 74(1-2), p. 3-13, 2000). The natural normal host for type A influenza virus is wild water birds such as duck and seagull. From the epidemiological studies of influenza virus infection in wild birds over the world, it was confirmed that all the existing 16 kinds of HA and 9 kinds of NA were found in wild birds (Selmons et al., Avian Dis., 18(1), p. 119-124, 1974). Avian influenza virus classified as type A is the zoonosis virus which is divided into three major groups (Alexander D J, Vet. Microbiol., 74(1-2), p. 3-13, 2000); which are non-pathogenic avian influenza that causes light respiratory symptoms when it infects chickens, low pathogenic avian influenza (LPAI) that causes 1~30% mortality and egg drop syndrome, and highly pathogenic avian influenza (HPAI) called "Bird Flu" that shows high lethality of at least 95%. Particularly, HPAI is classified as List A disease by OIE (Office International des Epizooties) and as 1$^{st}$ class contagious animal disease in Korea.

Since 1980s, HPAI has been reported world-widely including USA (1983), Australia (1985, 1992, 1994 and 1997), Mexico (1994), Pakistan (1994 and 2004), Hong Kong (1997 and 2001), Italia (1997 and 1999), Netherland (2003), Belgium (2003), Germany (2003), and Canada (2004). In addition, starting with Korea (December, 2003), almost all the East-South Asian and Far East Asian countries including Vietnam, Japan, Thailand, Cambodia, Laos, Indonesia, and China reported the break-out of serotype A/H5N1 HPAI all at the same time in 2004. In particular, HPAI broken out in Vietnam and Thailand, unlike typical HPAI broken out in Korea and Japan at that time that has been characterized as not being infectious to human, was confirmed as a mutant avian influenza (mutant A/H5N1 HPAI) that was infectious to human via contact with infected birds. As of March, 2004 in Vietnam, 15 out of 22 people infected with the mutant form by the contact with the infected birds were dead and 8 out of 11 people were also killed in Thailand as well, worrying all the countries. The frequency of HPAI outbreak is 10 times higher than before. Since 2001, HPAI outbreak has been reported every year world-widely. Therefore, it is required to develop a novel prevention method which is effective in controlling HPAI (Song C S et al., Korean J. Poult. Sci., 31(2), p. 129-136, 2004).

Some serotypes of influenza virus, which causes problems in birds, cause even death in human after developing flu symptoms. Some mutant forms originated from three serotypes of avian influenza virus such as A/H7N7, A/H9N2, and A/H5N1 so called "Hong Kong avian influenza" are assumed to be infectious to human. Therefore, studies on such mutant virus forms originated from the above three serotypes have been eagerly going on word-widely (Suarez D L et al., J. Virol., 72(8), p. 6678-6688, 1998).

In the meantime, novel influenza that has been now prevailing all over the world since it was first found in Mexico in spring of 2009 is influenza type A subtype H1N1 having type 1 hemagglutinin (H1) and type 1 neuraminidase (N1) (Hereinafter, the said novel influenza A virus is called '2009 N1H1 influenza virus'). The 2009 N1H1 influenza virus is a kind of virus in which genetic materials of influenza viruses originated from human, swine, and birds are mixed. At this time swine is called as "mixing vessel". Thus, it was first named as swine influenza. However, since there was no proof saying that this virus is directly delivered to human from infected swine or delivered to swine from infected human or related to swine whatsoever, WHO used to call it novel influenza A (H1N1). From the sequence analysis of 2009 N1H1 influenza virus, it was confirmed that HA gene includes a certain sequence that is infectious to human, suggesting the possibility of infecting human. HA gene does not contain dibasic amino acid, the typical amino acid of highly pathogenic virus, but comprises drug resistant gene against amantadine and rimantadine. The virus was also confirmed not to have any mutation in NS1 and PB2 genes in relation to pathogenicity, suggesting that the virus was not highly pathogenic. 2009 N1H1 influenza virus is infectious through respiratory system and is highly contagious compared with the conventional influenza A virus. The symptoms of this virus are similar to those of the conventional influenza virus, for example high fever, cough, etc. To prevent the infection, personal hygiene including hand-washing and wearing a mask is required. It is recommended to treat the virus infection to use antiviral agents such as Tamiflu and Relenza.

Once infected with influenza virus, each organ in respiratory system loses its resistance, resulting in the development of complications such as bronchitis, laryngopharyngitis, and pneumonia. Particularly, chronic disease patients, aged people, children, and long-term hospitalized patients are in high risk since their immunities are very weak. Therefore, studies to prevent influenza are going on in the aspects of biosecurity and influenza vaccine. However, to get vaccine shot, proper timing is important as well as the prediction of the kind of prevailing influenza virus, which are troublesome.

Efforts have been made world-widely to develop an antiviral agent. Up to date, lamibudine used for the treatment of HIV-1 and hepatitis B, gancyclovir used for the treatment of herpes virus infection, and ribavirin used for the treatment of respiratory syncytial virus infection and also used for the urgent care of diverse virus infections have been approved and now are on the market. In addition, amantadine approved for the treatment of influenza virus A and its analogue rimantadine, zanamivir (Relenza) artificially synthesized as an influenza virus neuraminidase inhibitor, and oseltamivir (TAMIFLU™) are also on the market. Amantadine and rimantadine are designed to inhibit the functions of M2 ion channel protein of influenza virus, which are representative antiviral agents suppressing in vivo proliferation of influenza virus. These two antiviral agents are only effective for serotype A influenza virus and not effective at all for serotype B influenza virus that does not contain M2 protein. There is another problem in using amantadine and rimantadine. That is, with the use of those drugs, a mutant virus is easily generated whose M2 ion channel protein is not affected by those drugs. Zanamivir and oseltamivir, developed to overcome the above problem, are designed to inhibit the functions of neuraminidase, which became representative antiviral agents inhibiting the proliferation of influenza virus in vivo. These two antiviral agents are known to be effective in inhibiting all of 16 kinds of serotype A influenza virus and all of serotype B influenza virus. However, zanamivir needs to be inhaled or injected intravenously, which is not an easy pathway. In the meantime, oseltamivir can be orally administered, but according to the recent reports, side effects such as vomiting and dizziness are accompanied with the oral administration and resistant virus has been also generated (Ward P et al., J. Antimicrob. Chemother., 55(suppl), p. i5-i21, 2005). Therefore, it is important to develop a safe natural agent along with the vaccine and therapeutic agents to increase human immunity and to reduce death rate upon pandemic of such virus.

To treat influenza in Oriental Medicine, different kinds of medicinal herbs are boiled together and the extract therefrom is used, which is exemplified by Insampaedoksan, Gumiganghwalsan, Galgeun-tang, Mahwang-tang, Daecheongryong-tang, Seungmagalgeun-tang, Chungjogupae-tang, Yihyangsan, and Baekhogainsam-tang. Many kinds of medicinal herbs are used, and these are more to increase immunity of human body than to act as an antiviral agent. Thus, it is urgent request to develop a novel drug to prevent and/or treat influenza virus-induced disease more fundamentally.

The present inventors investigated the effect of diverse medicinal herbs used in Oriental Medicine on the activity of influenza virus. As a result, the present inventors completed this invention by confirming that the herbal extract extracted from the mixture prepared by adding *Epimedium koreanum*, Lonicerae Flos, Polygala Root, and Saussurea lappa to the raw materials of Bangpungtongsungsan used for the treatment of cardiovascular disease such as hypertension and arteriosclerosis had excellent preventive and/or therapeutic effect on various kinds of influenza virus-induced diseases.

SUMMARY OF THE INVENTION

Technical Problem

It is an object of the present invention to provide a herbal extract extracted from the mixture prepared by adding *Epimedium koreanum*, Lonicerae Flos, Polygala Root, and *Saussurea lappa* to the raw materials of Bangpungtongsungsan, a composition, and a health food for the prevention and/or treatment of influenza virus-induced diseases comprising the said herb extract as an active ingredient.

Technical Solution

To achieve the above abject, the present invention provides a herbal extract extracted from the herb mixture including *Epimedium koreanum*, Lonicerae Flos, Polygala Root, *Saussurea lappa*, and raw materials of Bangpungtongsungsan such as Cnidium Rhizome, *Saposhnikovia divaricata*, Korean angelica, peony, Forsythia, *Menthae herba*, *Ephedra sinica*, *Erigeron canadensis* , *Rheum palmatum*, gypsum, *Platycodon grandiflorum*, *Scutellariae radix*, *Atractylodes macrocephala*, *Gardenia jasminoides*, *Schizonepeta rhizome*, ginger, talc, and *Glycyrrhiza uralensis* by using an organic solvent.

To prepare the herbal extract of the present invention, *Epimedium koreanum*, Lonicerae Flos, Polygala Root, and *Saussurea lappa* are firstly added to the raw materials of Bangpungtongsungsan such as Cnidium Rhizome, *Saposhnikovia divaricata*, Korean angelica, peony, Forsythia, *Menthae herba, Ephedra sinica, Erigeron canadensis, Rheum palmatum*, gypsum, *Platycodon grandiflorum, Scutellariae radix, Atractylodes macrocephala, Gardenia jasminoides, Schizonepeta rhizome*, ginger, talc, and *Glycyrrhiza uralensis*, to which an organic solvent, preferably water, is added by 2~10 times the volume of the herb mixture. Then, extraction is performed at 70° C.~125° C. for 1~10 hours or preferably for 3~4 hours. In addition to the said hot water extraction, enfleurage, reflux extraction, or ultrasonic extraction can be used. According to the preparation of the herbal extract of the present invention, 0.5~5 weight part of each Cnidium Rhizome, *Saposhnikovia divaricata*, Korean angelica, peony, Forsythia, *Menthae herba, Ephedra sinica, Erigeron canadensis, Rheum palmatum*, gypsum, *Platycodon grandiflorum, Scutellariae radix, Atractylodes macrocephala, Gardenia jasminoides, Schizonepeta rhizome*, ginger, talc, *Glycyrrhiza uralensis,* Lonicerae Flos, Polygala Root, and *Saussurea lappa* is added to 1 weight part of *Epimedium koreanum*. However, the mixing ratio can be out of the said range. Besides, any medicinal herbs generally used for the purpose of the prevention and/or treatment of cold or flu in Oriental Medicine can be added to the above mixture. In this invention, the said organic solvent is exemplified by water, $C_1$-$C_4$ alcohol, $C_1$-$C_4$ ketone, $C_1$-$C_4$ aldehyde and aqueous solution of alcohol, ketone or aldehyde. Among these, water is more preferred.

In this invention, the said influenza virus preferably has the serotype selected from the group consisting of H1N1, H1N2, H2N2, Human B, H3N2, H3N8, H5N1, H5N2, H5N3, H5N8, H5N9, H7N1, H7N2, H7N3, H7N4, H7N7, H9N2, and H10N7, and more preferably has the serotype selected from the group consisting of H1N1, H3N2, Human B, H5N1, H9N2, H7N1, and H7N2, and most preferably has the serotype of H1N1.

The herbal extract of the present invention can be administered orally or parenterally and be used in general forms of pharmaceutical formulation. That is, the herbal extract of the present invention can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing the said herbal extract with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations and suppositories. Water insoluble excipients and suspensions can contain propylene glycol, polyethylene glycol, vegetable oil like olive oil, injectable ester like ethylolate, etc. Suppositories can contain witepsol, macrogol, tween 61, cacao butter, laurin butter, glycerol, gelatin, etc.

The herbal extract of the present invention can be administered to mammals such as human, cattle, swine, horses, sheep, rats, and mice, and birds such as fowls and ducks by various pathways. For example, the possible administration pathway can be oral administration, rectal administration, intravenous injection, intramuscular injection, hypodermic injection, intrauterine injection or intracerebroventricular injection. The effective dosage of the herbal extract of the present invention can be determined according to absorption of an active ingredient, inactivation rate, excretion, age, gender, health condition, and severity of a disease. In general, the dosage for adult is 10~5,000 mg/kg per day and preferably 100~3,000 mg/kg per day, and administration frequency is preferably 1~6 times a day. The dosage unit can contain, for example, 1, 2, 3 or 4 individual doses or ½, ⅓ or ¼ of an individual dose. An individual dose preferably contains the amount of active compound which is administered in one application and which usually corresponds to a whole, ½, ⅓ or ¼ of a daily dose.

Since the herbal extract of the present invention is a natural substance and has no toxicity, it can be continuously administered at a high dose. The herbal extract of the present invention is evaluated to be a safe substance since its estimated $LD_{50}$ value is much greater than 5 g/kg in mice, which is confirmed by toxicity assay with mice tested via oral administration. In a preferred embodiment of the present invention, the herbal extract of the present invention demonstrated good clinical signs, and particularly when administered at a high dosage, the extract could eliminate influenza virus from the lung of the test animal (see FIGS. 1 and 2). Therefore, it was confirmed that the herbal extract of the present invention could be effectively used for the treatment of influenza virus.

The present invention also provides a health food for the prevention of influenza virus-induced disease or alleviation of its symptoms comprising the said herbal extract as an active ingredient. The health food herein indicates the food with improved functionality, compared with the general food, obtained by adding the herbal extract of the present invention thereto. The functionality herein indicates physical properties and physiological functions. When the herbal extract of the present invention is added to general food, physical properties and physiological functions of the food can be improved and such food improved in functions is described as 'health food' inclusively in this invention.

In this invention, the said influenza virus preferably has the serotype selected from the group consisting of H1N1, H1N2, H2N2, Human B, H3N2, H3N8, H5N1, H5N2, H5N3, H5N8, H5N9, H7N1, H7N2, H7N3, H7N4, H7N7, H9N2, and H10N7, and more preferably has the serotype selected from the group consisting of H1N1, H3N2, Human B, H5N1, H9N2, H7N1, and H7N2, and most preferably has the serotype of H1N1.

The herbal extract of the present invention can be added to health food for the prevention of influenza virus induced disease or alleviation of its symptoms. In that case, the herbal extract of the present invention can be added as it is or as mixed with other food components according to the conventional method. The mixing ratio of active ingredients can be regulated according to the purpose of use (prevention, health enhancement or treatment). In general, to produce health food or beverages, the herbal extract of the present invention is added preferably by up to 30 wt % and more preferably by up to 10 wt %. However, if long term administration is required for health and hygiene or regulating health condition, the content can be lower than the above but higher content can be accepted as well since the herbal extract of the present invention has been proved to be very safe.

The food herein is not limited. For example, the herbal extract of the present invention can be added to meats, sausages, breads, chocolates, candies, snacks, cookies, pizza, ramyuns, flour products, gums, dairy products including ice cream, soups, beverages, tea, drinks, alcohol drinks and vitamin complex, etc, and in wide sense, almost every food applicable in the production of health food can be included.

The composition for health beverages of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and glucose alcohols such as xilytole, sorbitol and erythritol. Besides, natural sweetening agents such as thaumatin and stevia extract, and synthetic sweetening agents such as saccharin and aspartame can be included as a sweetening agent. The content of the natural carbohydrate is preferably 0.01~0.04 g and more preferably 0.02~0.03 g in 100 ml of the herbal extract of the present invention.

In addition to the ingredients mentioned above, the herbal extract of the present invention can include in a variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, carbonators which used to be added to soda, etc. The herbal extract of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by 0.01~0.1 weight part per 100 weight part of the herbal extract of the present invention.

Advantageous Effect

The herbal extract of the present invention comprising Epimedium koreanum is very safe for human body because it is originated from the natural source, so that it can be used for the prevention and treatment of various influenza virus-induced diseases and alleviation of symptoms of those.

BRIEF DESCRIPTION OF THE DRAWINGS

The application of the preferred embodiments of the present invention is best understood with reference to the accompanying drawings, wherein.

DETAILED DESCRIPTION

Figure 1:
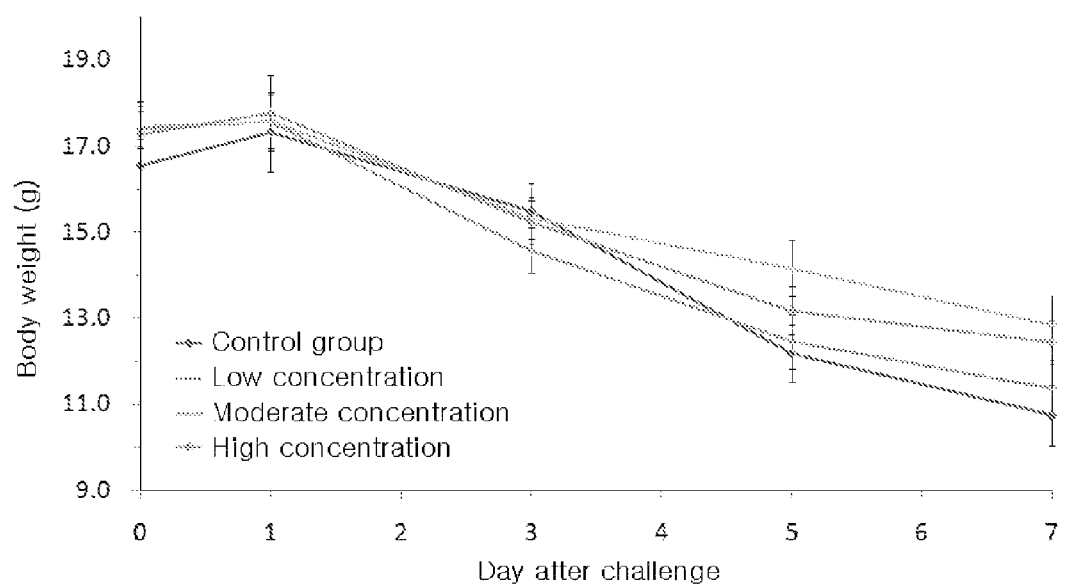
FIG. 1 is a graph illustrating the weight changes of mice after the administration of test material.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Preparation of Herbal Extract

All the medicinal herbs which were homegrown were purchased for the test. One l of water was added to approximately 49 g of the selected medicinal herbs having the composition of Table 1, which stood at room temperature for 1 hour. Then hot water extraction was performed at 100° C. for 3 hours, and as a result, approximately 100 ml of herbal extract was obtained. Approximately 9.6 g of freeze-dried material was obtained by freeze-drying the obtained herbal extract. The herbal extract or its freeze-dried material was used in this invention.

TABLE 1

| Law material | Weight(g) |
| --- | --- |
| Epimedium koreanum | 1.69 |
| Lonicerae Flos | 1.69 |
| Polygala Root | 1.69 |
| Saussurea lappa | 1.69 |
| Cnidium Rhizome | 1.69 |
| Saposhnikovia divaricata | 1.69 |
| Korean angelica | 1.69 |
| peony | 1.69 |
| Forsythia | 1.69 |
| Menthae herba | 1.69 |
| Ephedra sinica | 1.69 |
| Erigeron canadensis | 1.69 |
| Rheum palmatum | 1.69 |
| gypsum | 2.62 |
| Platycodon grandiflorum | 2.62 |
| Scutellariae radix | 2.62 |
| Atractylodes macrocephala | 1.31 |
| Gardenia jasminoides | 1.31 |
| Schizonepeta rhizome | 1.31 |
| ginger | 4.6 |
| talc | 6.37 |
| Glycyrrhiza uralensis | 4.5 |

EXAMPLE 2

Animal Test with Mice

The freeze-dried material of the herbal extract prepared in Example 1 was orally administered to the mice infected with influenza virus, followed by observation of the symptoms. Particularly, the mice infected with novel influenza virus isolated in Korea (A/Cheongju/o4/09) was orally administered with the freeze-dried material of the herbal extract prepared in Example 1 at a low concentration (low concentration administration group), at a moderate concentration (moderate concentration administration group), and at a high concentration (high concentration administration group), and administered with the control substance (control group). At this time, the low concentration administration group was treated with 0.478 g/kg of the extract which was as high as one day dosage of the extract, and the moderate concentration administration group was treated with 2.39 g/kg of the extract which was 5 times the one day dosage, and the high concentration administration group was treated with 4.78 g/kg of the extract which was 10 times the one day dosage. Each group had 10 mice. The test material was orally administered to the animals 9 times in total from the first day of influenza virus infection to the $8^{th}$ day. After the infection with novel influenza virus, weights of the animals were measured on day 1, day 3, day 5, and day 7. On day 1, day 3, day 5, day 7, and day 9, two mice of each group were sacrificed and virus titer was measured with their lung tissues by using chicken embryos. To do so, mouse lung tissue samples were homogenized in 1× PBS (phosphate buffered saline) containing antibiotics, and the homogenized tissues were centrifuged at 12,000 g. The supernatant was transferred to a new tube, which was then 10 fold-diluted. The diluted supernatant was inoculated to the fertilized egg containing 11 days old embryo, followed by measurement of virus. The result was presented as log 10 EID50/ml.

Figure 2:
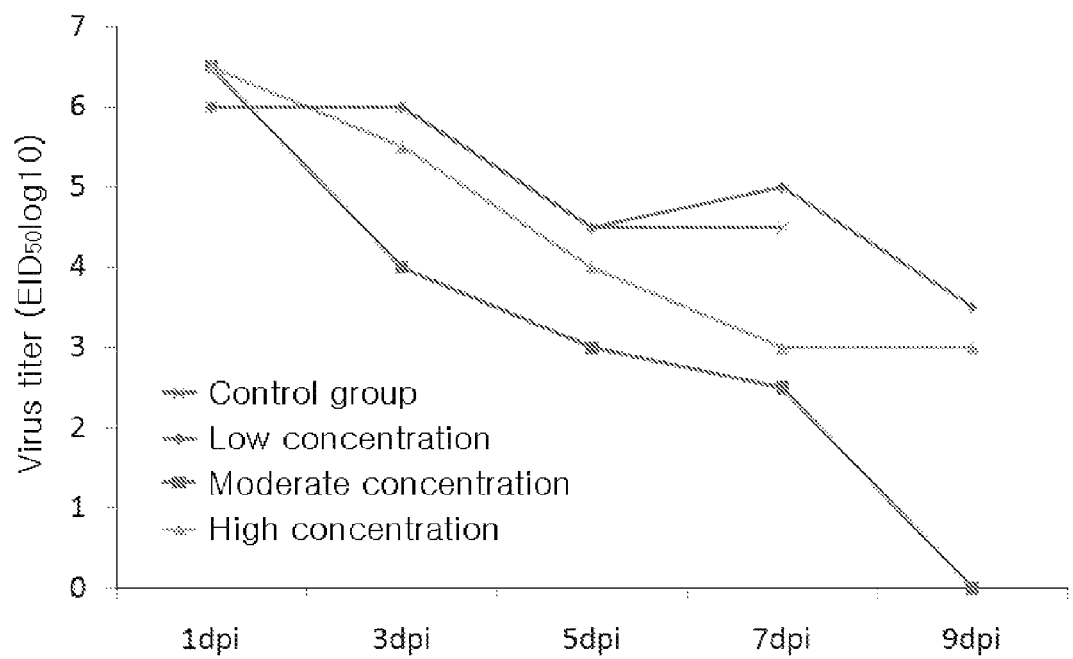
FIG. 2 is a graph illustrating the virus titer measured in lung tissues of mice after the administration of test material.

As a result, the weights of mice in the group administered with the herbal extract of the present invention were gradually reduced, which were not significantly different from those of the control, though (FIG. 1). The group administered with the herbal extract of the present invention demonstrated comparatively moderate symptoms, compared with the control group, and no death was observed until day 9. In particular, in the moderate concentration administration group, it was confirmed that influenza virus was eliminated from the lung of the infected mouse (FIG. 2). From the above result was confirmed that the herbal extract of the present invention was very effective in the treatment of influenza virus infection.

EXAMPLE 3

Acute Toxicity Test

Four weeks old specific pathogen-free (SPF) ICR mice, provided from Orient, Co., Ltd., Korea, were used for the following acute toxicity test. The herbal extract of Example 1 was prepared at 5 different concentrations (5 g/kg, 4,000 mg/kg, 3,200 mg/kg, 2,560 mg/kg, and 0 mg/kg). Each concentration of the herbal extract was administered to 5 female and 5 male mice of each group. After one time oral administration, death, clinical symptoms, and weight changes of the animals were observed (before and 1, 3, 7, and 14 days after the administration). And any abnormal signs in the gastrointestinal organs of chest and abdomen were checked with eyes during autopsy.

The results showed that the extract did not cause any specific clinical symptoms, weight change, or death in mice. No change was observed in hematological tests, biochemical tests of blood, and autopsy. Therefore, the herbal extract of the present invention is evaluated to be a safe substance since it does not cause any toxic change in mice up to the level of 5 g/kg and its estimated $LD_{50}$ value is much greater than 5 g/kg in mice.

MANUFACTURING EXAMPLE 1

Preparation of Pharmaceutical Composition Containing Herbal Extract

<1-1> Preparation of Syrups

Syrups containing the herbal extract of the present invention by 2% (weight/volume) as an effective ingredient were prepared as follows. The herbal extract powder prepared in Example 1, saccharin, and sucrose were dissolved in 80 g of warm water. The mixture was cooled down, to which a mixture of glycerin, saccharin, flavors, ethanol, sorbic acid, and distilled water was added. Water was added to the mixture, making a total volume of 100 ml.

The constituents of the syrups are as follows.

| | |
|---|---|
| Herbal extract | 2 g |
| Saccharin | 0.8 g |
| Sucrose | 25.4 g |
| Glycerin | 8.0 g |
| Flavor | 0.04 g |
| Ethanol | 4.0 g |
| Sorbic acid | 0.4 g |
| Distilled water | Proper amount |

<2-2> Preparation of Tablets

Tablets containing 15 mg of the herbal extract of the present invention as an active ingredient were prepared as follows.

250 g of the herbal extract prepared in Example 1, 175.9 g of lactose, 180 g of potato-starch, and 32 g of colloidal silicic acid were all mixed together. 10% gelatin solution was added to the mixture, which was then pulverized and filtered with 14-mesh sieve. The pulverized mixture was dried, to which 160 g of potato-starch, 50 g of talc, and 5 g of magnesium stearate were added to prepare tablets.

<1-3> Preparation of Injectable Solution

Injectable solutions containing 10 mg of the herbal extract of the present invention as an active ingredient were prepared as follows. 1 g of the herbal extract prepared in Example 1, 0.6 g of sodium chloride, and 0.1 g of ascorbic acid were dissolved in distilled water to make 100 ml of solution. The solution was put in a bottle and heated at 20° C. for 30 minutes for sterilization.

<1-4> Preparation of Powders

Powders were prepared by mixing 20 mg of the herbal extract prepared in Example 1, 100 mg of lactose, and 10 mg of talc, which were filled in airtight packs according to the conventional method for preparing powders.

<1-5> Preparation of Capsules

Capsules were prepared by mixing 10 mg of the herbal extract prepared in Example 1, 3 mg of crystalline cellulose, 14.8 mg of lactose, and 0.2 mg of magnesium stearate, which were filled in gelatin capsules according to the conventional method for preparing capsules.

MANUFACTURING EXAMPLE 2

Preparation of Healthy Food

<2-1> Preparation of Food

Foods containing the herbal extract of the present invention were prepared as follows.

1. Preparation of Spices for Cooking

Health enhancing spices for cooking were prepared with 20~95 wt % of the herbal extract of the present invention according to the conventional method.

2. Preparation of Tomato Ketchup and Sauce

Health enhancing tomato ketchup or sauce was prepared by mixing 0.2~1.0 wt % of the herbal extract of the present invention with tomato ketchup or sauce according to the conventional method.

3. Preparation of Flour Foods

The herbal extract of the present invention was added to the flour by 0.5~5.0 wt %. Health enhancing foods such as bread, cake, cookies, crackers and noodles were prepared with the flour mixture according to the conventional method.

4. Preparation of Soups and Gravies

The herbal extract of the present invention was added to soups and gravies by 0.1~5.0 wt %. Health enhancing meat products, soups and gravies were prepared with this mixture by the conventional method.

5. Preparation of Ground Beef

Health enhancing ground beef was prepared by mixing 10 wt % of herbal extract of the present invention with ground beef according to the conventional method.

6. Preparation of Dairy Products

The herbal extract of the present invention was added to milk by 5~10 wt %. Health enhancing dairy products such as butter and ice cream were prepared with the milk mixture according to the conventional method.

7. Preparation of Sun-Sik

Brown rice, barley, glutinous rice, and Yulmu (Job's tears) were gelatinized according to the conventional method, dried and pulverized to obtain 60-mesh powders. Black soybean, black sesame and wild sesame were steamed and dried according to the conventional method and pulverized to obtain 60-mesh powders. The herbal extract of the present invention was concentrated under reduced pressure, spray-dried and pulverized to obtain 60-mesh dry powders. Sun-Sik was prepared by mixing the dry powders of the grains, seeds and the herbal extract of the present invention according to the below ratio.

Grains (brown rice: 30 wt %, Yulmu: 15 wt %, barley: 20 wt %),

Seeds (wild sesame: 7 wt %, black soybean: 8 wt %, black sesame: 7 wt %),

Dry powders of the herbal extract (3 wt %),

*Ganoderma lucidum* (0.5 wt %),

*Rehmannia glutinosa* (0.5 wt %)

<2-2> Preparation of Beverages

1. Preparation of Carbonated Beverages

Syrup was prepared by mixing the herbal extract of the present invention with sugar (5-10%), citric acid (0.05-0.3%), caramel (0.005-0.02%), vitamin C (0.1-1%), and purified water (79-94%). The syrup was sterilized at 85-98° C. for 20-180 seconds, and then mixed with cooling water at the ratio of 1:4. Carbon dioxide was injected thereto by 0.5-0.82% to prepare carbonated beverages containing the herbal extract of the present invention.

2. Preparation of Health Beverages

The herbal extract of the present invention was mixed with liquid fructose (0.5 wt %), oligosaccharide (2 wt %), sugar (2 wt %), salt (0.5 wt %), and water (75 wt %). After mixing completely, the mixture was sterilized instantly and filled small containers such as glass bottles, pet bottles, etc, to prepare health beverages.

3. Preparation of Vegetable Juice

Health enhancing vegetable juice was prepared by adding 5 g of the herbal extract of the present invention to 1,000 ml and of tomato or carrot juice according to the conventional method.

4. Preparation of Fruit Juice

Health enhancing fruit juice was prepared by adding 1 g of the herbal extract of the present invention to 1,000 ml of apple or grape juice according to the conventional method.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A pharmaceutical composition for treating influenza consisting essentially of therapeutically effective amounts of extracts of Cnidium Rhizome, *Saposhnikovia divaricata*, Korean angelica, peony, Forsythia, *Menthae herba, Ephedra sinica, Erigeron canadensis, Rheum palmatum*, gypsum, *Platycodon grandiflorum, Scutellariae radix, Atractylodes macrocephala, Gardenia jasminoides, Schizonepeta rhizome*, ginger, talc, *Glycyrrhiza uralensis, Epimedium koreanum*, Lonicerae Flos, Polygala Root and *Saussurea lappa*.

* * * * *